United States Patent [19]

Jacobs et al.

[11] Patent Number: 4,670,620
[45] Date of Patent: Jun. 2, 1987

[54] PROCESS FOR OBTAINING ETHYLENE FROM ETHANOL

[75] Inventors: Julia M. Jacobs, Malle; Pierre A. Jacobs, Gooik; Jan B. Uytterhoeven, Heverlee, all of Belgium

[73] Assignee: De Belgische Staat-l'Etat Belge, Brussels, Belgium

[21] Appl. No.: 902,011

[22] Filed: Aug. 28, 1986

Related U.S. Application Data

[63] Continuation-in-part of Ser. No. 770,135, Aug. 28, 1985, abandoned.

[30] Foreign Application Priority Data

Aug. 28, 1984 [LU] Luxembourg .......................... 85515

[51] Int. Cl.$^4$ ................................................ C07C 1/24
[52] U.S. Cl. .................................. 585/640; 585/408; 585/469; 585/639
[58] Field of Search ............... 585/640, 639, 638, 408, 585/469, 733

[56] References Cited

U.S. PATENT DOCUMENTS 4,052,479 10/1977 Chang et al. ......................... 585/640
4,134,926 1/1979 Tsao et al. ............................ 585/640

FOREIGN PATENT DOCUMENTS 175399 3/1986 European Pat. Off. ............ 585/639
3240870 5/1984 Fed. Rep. of Germany ...... 585/640

OTHER PUBLICATIONS

Oudjams et al., Applied Catalysis, vol. 3, 109–115 (1982).
Chemical Abstract 102:9288g (1985).
Chemical Abstract 96:180744j (1982).

Primary Examiner—Asok Pal
Attorney, Agent, or Firm—Sughrue, Mion, Zinn, Macpeak and Seas

[57] ABSTRACT

This invention relates to a process for obtaining ethylene from anhydrous or aqueous ethanol by means of a catalyst of the zeolite type containing a silicate of a metal M1 having a valence of 3 and 4 and a tetraedric coordination and containing possibly another charge compensating metal M2 selected among the elements of the Ia, Ib, IIa, IIb, IIIa, IIIb, IVa, IVb, Va, VIb, VIIb and VIII groups of the Mendeljev Table. As examples of M2 metals, the alkaline metals, the alkaline-earth metals and the lanthanides may be cited.

According to the invention, anhydrous or aqueous ethanol is contacted with a catalyst of the above type, in which the ratio (M1−M2/n)/(Si+M1)(in which II is the valence of said other metal) is at most equal to 1.5%. The temperature of the catalyst and the contact time of ethanol with said catalyst are such that the conversion rate of ethanol into ethylene is about 100% and the carbon selectivity for ethylene is at least equal to about 99% by weight.

12 Claims, No Drawings

PROCESS FOR OBTAINING ETHYLENE FROM ETHANOL

This is a continuation-in-part of application Ser. No. 770,135, filed Aug. 28, 1985, now abandoned.

PRIOR ART

It is known from U.S. Pat. No. 3,894,107 to use catalysts of the crystalline aluminosilicate zeolite type having low alumina contents, such as silica/alumina ratios of at least 12, for converting various organic compounds, such as ethanol, into aliphatic hydrocarbons, such as ethylene.

Moreover, the European patent application No. 0 022 640 describes a process for converting ethanol and ethylene into higher aliphatic hydrocarbons and/or for converting ethanol into ethylene. In this process ethanol is contacted with a zeolite catalyst having a silica/alumina ratio of more than 10, this catalyst being a ZSM-5 catalyst which is treated by a hydrogen halide or an organic halide capable of releasing a hydrogen halide or mineral acid, in order to improve the catalytic performance of the zeolite.

The French Pat. No. 2,306,981 and the corresponding U.S Pat. Nos. 4,025,575 and 4,025,576 also disclose a process for converting into olefins starting materials consisting of alcohols and/or esters containing no more than 4 carbon atoms per alkyl group, by contacting said starting materials (which may be ethanol) with a catalyst comprising a crystalline aluminosilicate zeolite having a constraint index comprised between 1.0 and 12.0, a silica/alumina ratio comprised between 12 and 3.000 and a crystalline density, in protonated form, somewhat lower than 1.6, the starting material and the catalyst being contacted under severity conditions which are sufficiently low for reducing the capacity of the catalyst to produce an aromatisation.

The products obtained by these known processes are higher aliphatic hydrocarbons containing more carbon atoms than the starting alcohol, or a mixture of hydrocarbons containing noticeable amounts of several olefins.

BRIEF DESCRIPTION OF THE INVENTION

It has now been discovered that some catalysts of the crystalline zeolite type can be used for obtaining substantially pure ethylene, as sole hydrocarbon, from pure ethanol or from aqueous solutions of ethanol, even very diluted ethanol solutions, the conversion rate of the ethanol being of about 100%.

Moreover, it has been found that the catalysts of the zeolite type selected for the process according to this invention are remarkably stable, even in the presence of important amounts of water in the starting ethanol solution.

The process according to the invention for obtaining ethylene from anhydrous ethanol or aqueous ethanol by means of a catalyst of the zeolite type containing a silicate of a metal M1 having a valence equal to 3 and a tetraedric coordination and containing possibly another charge compensating metal M2 selected, for example, among the alkaline metals, the alkaline-earth metals and the lanthanides is characterized by using a catalyst of the above type containing a proportion of a metal M1 such that the molar ratio $(M1-M2/n)/(Si+M1)$, in which n is the valence of said other metal, is at most of about 1.5% and by contacting anhydrous ethanol or aqueous ethanol with this catalyst at such a temperature and contact time that the conversion rate of ethanol is close to 100% and the ethylene carbon selectivity is at least equal to about 99% by weight.

DETAILED DESCRIPTION OF THE INVENTION

According to a feature of the invention, a catalyst as defined above, in which the metal M1 is aluminium, bromine, beryllium, chromium or iron or a mixture of aluminium and of at least another of these metals is used in the process.

The catalyst used in the process according to the invention contains preferably aluminium as metal M1, preferably without metal M2.

In general, the molar ratio $(M1-M2/n)/(Si+M1)$ of the catalyst used in the process according to this invention is preferably comprised between about 0.01% and about 1%.

The zeolites have preferably a particle size of at least 0.5 micron. This particle size may vary between wide limits and may reach, for example, 300 microns.

In a preferred embodiment the catalysts used according to this invention are of the ZSM-5 type and preferably at least partially under hydrogen form.

Although the catalysts used in the process according to the invention are preferably of the ZSM-5 type, as described in U.S Pat. No. 3,702,886, these catalysts may also be of the following types: ZSM-11 (as described in U.S. Pat. No. 3,709,979 and ZSM-48 (as described in European Pat. No. 0 015 132) and even of the ferrierite type (as described in European Pat. No. 0 012 473) and of the "Faujasite" type (as described in U.S. Pat. No. 3,130,007).

The M1 metal content of the catalysts, expressed by the above molar ratio, represents the amount of metal M1 which is present in the rigid anionic structure of the zeolite crystal, except the metal M1 contained in a binder or in cationic or other form. This content of the metals M1 and/or M2 is determined by analysis, for example by atomic absorption.

Said catalysts have a hydrophobic character which is advantageous for the conversion of ethanol into ethylene.

Substantially pure ethylene can be obtained by the process according to this invention from anhydrous or aqueous ethanol, for example from industrial alcohol containing about 96% by weight of ethanol or from a fermentation liquor which may contains only 4% by weight of ethanol.

The catalyst may be used in different ways in the process according to the invention. Thus, the catalyst may be used as a fixed bed, a fluidized bed or several layers of carried catalyst; the catalyst may possibly be used as an extruded product.

The anhydrous or aqueous ethanol is contacted, in gaseous or vapor phase, with the catalyst, possibly in the presence of an inert gas, such as nitrogen or helium. This gas may be recycled, if desired.

The terms "conversion rate", as used herein, mean the ratio in percents of the amount of converted ethanol to the amount of ethanol fed.

For obtaining a conversion rate of ethanol of almost 100% and a carbon selectivity for ethylene at least equal to about 99% by weight, in accordance with the invention, the temperature of the catalyst and the flow rate of the starting liquid must be adjusted in accordance with the particular type of catalyst which is used for the reaction.

The temperature at which the catalyst is maintained for the quantitative conversion of ethanol into ethylene may vary between wide limits, namely between 400 K and 800 K, preferably between about 500 and 700 K, this temperature being the maximum temperature reached in the catalyst bed.

The flow rate of the starting ethanol-containing liquor passed through the catalyst bed may also vary between wide limits. Thus, said contact time determined by the liquid hourly space velocity (LHSV) which corresponds to the volume of ethanol contacted with the catalyst per hour and per volume of catalyst may vary between 0.05 and 10 hours$^{-1}$, preferably between 0.1 and 5 hours$^{-1}$.

The optimum values of the temperature of the catalyst and of the contact time of the starting ethanol-containing liquor can be easily determined by experiments, taking into account the ethanol content of the starting liquor and the particular type of catalyst used with this liquor, in order to obtain a conversion rate of almost 100% and an ethylene carbon selectivity of at least 99% by weight in accordance with this invention.

When the process according to the invention is carried out on a large scale, preliminary tests are made in which the temperature of the catalyst and/or the flow rate of the starting ethanol-containing liquor are gradually increased until these temperature and contact time values are such that all the ethanol contained in said starting liquor is quantitatively dehydrated and the ethylene carbon selectivity is at least equal to about 99% by weight.

After a reaction, a mixture of water and of an organic phase is obtained; the organic phase can be easily separated from the aqueous phase by mere cooling, so that an organic phase containing almost exclusively ethylene is recovered.

The ethanol-containing liquor used in the process according to the invention may be manufactured either from biomass fermentation or synthesized from coal or petroleum synthesized syngas containing ethanol in an anhydrous form or in a more or less concentrated form before submitting the ethanol-containing liquor to the catalytic process of conversion of ethanol into ethylene in accordance with the present invention.

Substantial energy savings are possible when the process according to the invention is carried out, since the ethanol-containing starting liquor may have a low ethanol content the latter being almost completely converted into ethylene, due to the remarkable selectivity of the catalysts used in accordance with the invention.

In a particularly advantageous embodiment of the process according to the invention, this process is applied to a fermentation medium containing small amounts of ethanol; these amounts may be only of about 4% by weight.

Applicant does not know catalytic processes in which the ethanol contained in industrial fermentation liquors is selectively and quantitatively dehydrated and converted into ethylene with remarkable yields.

The process according to the present invention may be carried out at pressures of the starting ethanol-containing liquor and of the inert gas possibly used as diluent comprised between 1 and 10 atmospheres, although it is preferred to work at the atmospheric pressure.

The content of aluminium or other metal M1 of the catalysts used in the process according to the invention has been selected after many tests, so as to confer to said catalysts such an acidity that they catalyse selectively the deshydration reaction of ethanol into ethylene, said acidity being however not too high, for example to catalyse cracking or cyclization reactions which need larger activation energies. The catalysts used in the process according to the invention are not deactivated by the deposit of coke and have a high thermal and hydrothermal stability. Even in the presence of substantial amounts of water, the catalysts do not loose their catalytic activity or selectivity during a long time on stream.

EXAMPLES

The following examples illustrate the invention.

In these examples, it is shown that it is possible to obtain a conversion rate of ethanol of almost 100% and an ethylene carbon selectivity at least equal to about 99% by weight, in each case where a catalyst of the crystalline zeolite type is used, in which the ratio $(M1-M2/n)/(Si+M1)$ is lower or equal to about 1.5%. On the contrary, several examples show that it is not possible to obtain such a quantitative conversion rate as well as such a selectivity of more than 99% by weight, when a catalyst in which said ratio is of more than 1.5% is used.

The art worker was not able to predict that, by selecting a catalyst of the zeolite type as defined above, it would be possible to obtain a conversion rate of ethanol of almost 100% and a carbon selectivity for ethylenic of more than 99% by weight, in all cases where the above-said ratio is equal or lower than 1.5% for the catalyst used. These remarkable conversion rate and selectivity may be obtained even when said ratio is far below 1.5%, for example when this ratio is of 0.1% or even less, whatever be the ethanol content of the used ethanol-containing liquor.

EXAMPLE 1

Preparation of a H-ZSM-5 catalyst having a molar ratio $(M1-M2/n)/(Si+M1)$ of 1.62%

An aqueous solution of sodium silicate (silica source) has been added to an aqueous solution of tetrapropyl-ammonium hydroxide so as to obtain a solution (1) containing 40 ml of sodium silicate and 1.89 g of tetrapropylammonium hydroxide in 38 ml of water.

This solution (1) has been mixed (vigorous stirring) with a solution (2) consisting of 0.333 g of sodium aluminate dissolved in 10 ml of water.

The pH of the mixture has been adjusted to a value of 10 by adding concentrated sulfuric acid.

After addition of 40 ml of water, a gel having the following molar composition has been obtained: $0.5(R_2O); 5(Na_2O); 0,2(Al_2O_3); 24(SiO_2); 1000(H_2O)$ in which R represents the organic tetrapropylammonium cation.

This gel has been stirred in autoclaves at a temperature of 432 K during 3 days and the obtained product has then been washed, dried in the presence of air and calcined also in the presence of air at a temperature of 823 K during 12 hours.

The obtained zeolite has then been ion exchanged at a temperature of 353 K with 0.5M hydrochloric acid, at a liquid/solid ratio of 50 under continuous stirring for 1 hour.

After washing and drying, an hydrophobic crystalline catalyst having a ratio $Al/Si+Al$ of 1.62% has been obtained, the crystals having a size of about 4 microns. Since this catalyst does not contain sodium (M2), this ratio is (M1)/(Si+M1), where M1 is aluminium.

EXAMPLE 2

Conversion of ethanol by means of the catalyst of example 1

A sample of the catalyst of example 1 has been used for the dehydration reaction of ethanol into ethylene in the presence of water.

The catalyst has been charged to a tubular reactor of the continuous flow type and used without pretreatment.

The starting solution was an aqueous solution containing 90% by weight of absolute ethanol (i.e. ethanol containing more than 99.5% of ethanol)(ethanol U.C.B., Belgium).

This solution has been passed, in gaseous phase, over the catalyst at a liquid hourly space velocity (LHSV) of 0.31 hour$^{-1}$ together with 15 moles of dry helium (used as diluent) per mole of ethanol. The contact time of the reagent with the catalyst was 1.8 seconds.

The reaction was carried out at atmospheric pressure and the temperature was gradually increased from about 450 K to 570 K.

The reaction products have been analyzed on-line by gaseous chromatography.

It has been found that the catalyst was not deactivated during the treatment.

The working conditions and the results of the analysis are given in the following table 1. This table shows:
the temperatures;
the space velocity of the reagent (LHSV);
the conversion percentage or rate;
the distributions in % by weight of hydrocarbons.

The conversion rate has been expressed as follows:

$$\frac{\text{amount in g of converted } C_2H_5OH}{\text{amount in g of supplied } C_2H_5OH} \times 100$$

TABLE 1

CATALYST: H—ZSM-5 (Al/Si + Al % = 1,62)

| REACTION CONDITIONS | | | | | | |
|---|---|---|---|---|---|---|
| Temperature (K) | 449 | 472 | 496 | 520 | 544 | 569 |
| LHSV (1/hr) | 0.31 | 0.31 | 0.3 | 0.31 | 0.31 | 0.31 |
| Conversion (%) | 32.2 | 50.3 | 70.0 | 99.6 | 99.7 | 99.8 |
| DISTRIBUTION OF THE PRODUCTS (% by weight) | | | | | | |
| Diethylether | 75.9 | 57.9 | 22.2 | 0.0 | 0.0 | 0.0 |
| Water | 20.7 | 25.1 | 33.7 | 39.1 | 39.2 | 39.2 |
| Hydrocarbons | 3.4 | 17.0 | 44.1 | 60.9 | 60.8 | 60.8 |
| CO* | 0.0 | 0.0 | 0.0 | 0.0 | 0.0 | 0.0 |
| CO$_2$* | 0.0 | 0.0 | 0.0 | 0.0 | 0.0 | 0.0 |
| DISTRIBUTION OF THE HYDROCARBONS (% by weight) | | | | | | |
| Methane | 0.0 | 0.0 | 0.0 | 0.0 | 0.0 | 0.0 |
| Ethylene | 90.7 | 97.4 | 98.0 | 73.2 | 55.6 | 43.5 |
| Ethane | 0.0 | 0.0 | 0.0 | 0.0 | 0.0 | 0.0 |
| Propylene + propane | 0.0 | 0.0 | 0.2 | 3.7 | 6.2 | 8.7 |
| Butanes | 2.2 | 0.6 | 0.6 | 2.4 | 3.8 | 5.9 |
| Butenes | 0.0 | 0.1 | 0.2 | 5.0 | 8.7 | 10.7 |
| Pentanes | 0.0 | 0.0 | 0.1 | 1.9 | 2.7 | 3.5 |
| Pentenes | 0.0 | 0.0 | 0.0 | 3.2 | 5.5 | 6.0 |
| C5+ | 7.1 | 1.9 | 0.9 | 10.6 | 17.5 | 21.7 |
| % iso in C$_4$ | 100.0 | 82.1 | 55.5 | 57.9 | 61.4 | 64.8 |
| C$_5$+ aromatics | 89.0 | 84.1 | 76.1 | 24.9 | 39.7 | 49.0 |

*Undetected compounds.

The maximum theoretical conversion of ethanol into hydrocarbons and water is respectively 61% by weight and 39% by weight. Table 1 shows that this result is obtained at a temperature of 520 K.

At higher temperatures, the conversion rate of ethanol into hydrocarbons was maintained, but larger amounts of products other than ethylene were obtained.

The selectivity of the catalyst for the formation of ethylene or the carbon selectivity for ethylene was only relatively high, the maximum selectivity being of 98% by weight with a conversion rate of 70% at a temperature of 496 K.

When higher conversion rates have been obtained, the formation of by-products (other products than ethylene) became important and the ethylene carbon selectivity of the catalyst decreased quickly.

It is not possible to obtain both a conversion rate of almost 100% and an ethylene carbon selectivity of more than 99% by weight with the catalyst used in the present example, although the ratio Al/Si+Al is only slightly higher than the maximum of 1.5%.

EXAMPLE 3

Preparation of a H-ZSM-5 catalyst having a ratio (M1−M2/n)/(Si+M1)

The following starting solutions have been used:
solution (1):
20 grams of SiO$_2$ (aerosil) in 830 ml of 1N tetrapropylammonium bromide (TPABr).
(b) 5.32 g of NaOH in 10 ml of water;
4.66 g of NaOH in 10 ml of water;
solution (2): 1.24 g de Al(NO$_3$)$_3$.9 H$_2$O in 10 ml of water.
solution (3): 610 g of glycerol.

To solution (1), obtained by mixing first (a) and (b) and then (c), solution (2) has first been added. To the stirred mixture, solution (3) was then added.

The obtained mixture was crystallized in autoclaves during at least 4 to 5 days at a temperature of 423 K, while stirring.

The obtained solid product was separated from the supernatant liquid solution by filtration, washed with water and dried.

The X-ray diffraction analysis of the product has shown the product consisted of 100% ZSM-5 zeolite.

On a molar basis, the reaction mixture had the following composition: 100 SiO$_2$/Al(NO$_3$)$_3$;13 NAOH; 83 TPABr; 13 NH$_4$OH; 662 C$_3$H$_5$ (OH)$_3$.

The alkaline product has been activated by removing the organic TPA cations, by calcination in the presence of air at a temperature of 823 K during 12 hours.

The H form of the catalyst has been obtained by ion exchange with 0.5M hydrochloric acid at a temperature of 353 K during 1 hour, the medium being stirred, the liquid/solid ratio being of 50.

Crystals having a particle size of 5 to 6 microns have been obtained by filtration under vacuum, washing and drying the H-form of the catalyst.

Based on the results of the atomic absorption, the catalyst did not contain sodium (M2). The molar ratio (M1)/Si+M1), where M1 is aluminium, is of 1.0%.

EXAMPLE 4

Conversion of ethanol into ethylene by means the catalyst of Example 3

A solution containing 90% by weight of ethanol and 10% by weight of water has been contacted with a sample of the catalyst of example 3, the reaction conditions being similar to those described in example 2.

The working conditions and the products obtained at six different temperatures are shown in the following table 2.

TABLE 2

CATALYST: H—ZSM-5 (Al/Si + Al % = 1,0)

| REACTION CONDITIONS | | | | | | |
|---|---|---|---|---|---|---|
| Temperature (K) | 449 | 474 | 498 | 521 | 544 | 566 |
| LHSV (1/hr) | 0.31 | 0.31 | 0.31 | 0.31 | 0.31 | 0.31 |
| Conversion (%) | 16.4 | 32.9 | 60.9 | 100.0 | 100.0 | 100.0 |
| DISTRIBUTION OF THE PRODUCTS (% by weight) | | | | | | |
| Diethylether | 80.4 | 71.1 | 21.0 | 0.0 | 0.0 | 0.0 |
| Water | 19.6 | 21.8 | 34.0 | 39.1 | 39.0 | 39.1 |
| Hydrocarbons | 0.0 | 7.1 | 45.0 | 60.9 | 61.0 | 60.9 |
| CO* | 0.0 | 0.0 | 0.0 | 0.0 | 0.0 | 0.0 |
| $CO_2$* | 0.0 | 0.0 | 0.0 | 0.0 | 0.0 | 0.0 |
| DISTRIBUTION OF THE HYDROCARBONS (% by weight) | | | | | | |
| Methane | 0.0 | 0.0 | 0.0 | 0.0 | 0.0 | 0.0 |
| Ethylene | 0.0 | 99.1 | 99.5 | 99.6 | 88.6 | 77.2 |
| Ethane | 0.0 | 0.0 | 0.0 | 0.0 | 0.0 | 0.0 |
| C3 + C4 | 0.0 | 0.9 | 0.1 | 0.0 | 7.6 | 11.8 |
| Pentanes | 0.0 | 0.0 | 0.0 | 0.1 | 1.0 | 1.1 |
| Pentenes | 0.0 | 0.0 | 0.0 | 0.0 | 1.6 | 2.0 |
| C5+ | 0.0 | 0.0 | 0.4 | 0.3 | 1.2 | 7.9 |
| % C5+ aromatics | 0.0 | 0.0 | 0.0 | 0.0 | 0.0 | 83.0 |

*Undetected compounds

When the results of the use of the H-ZSM-5 catalyst having a ratio Al/Si+Al of 1.0% (table 2) are compared to those of the use of the H-ZMS-5 catalyst having a ratio Al/Si+Al of 1.62% (Example 2 - table 1), it appears that the selectivity of the catalyst of example 3 in respect of the formation of ethylene is higher and that less by-products are formed. The maximum selectivity (99.6%) for $C_2H_4$ (ethylene) and a conversion rate of 100% have been obtained at a temperature of 512 K.

EXAMPLE 5

Preparation of a H-ZSM-5 catalyst having a ratio (M1−M2/n)/(Si+M1) of 0.2%

This catalyst was prepared in the manner described in example 3, except that the aluminium content was changed by adding the adjusted amount of $Al(NO_3)_3 \cdot 9 H_2O$ to the same amounts of $SiO_2$, NaOH and TPABr.

The molar composition of the synthesis mixture was as follows: 500 $SiO_2$/Al $(NO_3)_3$; 12 NaOH; 83 TPABr; 13 $NH_4OH$; 662 $C_3H_5(OH)_3$.

The X-ray analysis has shown that the product consisted of 100% ZSM-5 zeolite.

The ion-exchange with the ammonium cation has been obtained by refluxing the catalyst in an excess of 1N ammonium chloride during 1 hour.

The hydrogen form of the catalyst has been obtained by calcining the catalyst in the presence of air at a temperature of 723 K during 1 hour.

A H-ZSM-5 catalyst containing no sodium and having a molar ratio (M1)/(Si+M1) equal to 0.2% (M1 being aluminium) has been obtained (size of the crystals: 3 to 5 microns).

EXAMPLE 6

Conversion of ethanol into ethylene by means of the catalyst of example 5

The working conditions were the same as in example 2, the starting reagent being an aqueous solution containing 90% by weight of ethanol.

The following table 3 shows the working conditions and the products obtained at different reaction temperatures.

TABLE 3

CATALYST: H—ZSM-5 (Al/Si + Al % = 0.2)

| REACTION CONDITIONS | | | | | | |
|---|---|---|---|---|---|---|
| Temperature (K) | 440 | 463 | 488 | 519 | 544 | 565 |
| LHSV (1/hr) | 0.31 | 0.31 | 0.31 | 0.31 | 0.31 | 0.31 |
| Conversion (%) | 9.3 | 26.1 | 47.5 | 100.0 | 100.0 | 100.0 |
| DISTRIBUTION OF THE PRODUCTS (% by weight) | | | | | | |
| Diethylether | 80.1 | 69.6 | 31.3 | 0.0 | 0.0 | 0.0 |
| Water | 18.5 | 21.7 | 31.2 | 39.0 | 39.0 | 39.0 |
| Hydrocarbons | 0.0 | 8.1 | 37.1 | 60.8 | 60.8 | 60.8 |
| CO | 1.4 | 0.6 | 0.4 | 0.2 | 0.2 | 0.2 |
| $CO_2$ | 0.0 | 0.0 | 0.0 | 0.0 | 0.0 | 0.0 |
| DISTRIBUTION OF THE HYDROCARBONS (% by weight) | | | | | | |
| Methane | 0.0 | 0.0 | 0.0 | 0.0 | 0.0 | 0.0 |
| Ethylene | 0.0 | 100.0 | 100.0 | 99.4 | 91.9 | 85.8 |
| Ethane | 0.0 | 0.0 | 0.0 | 0.0 | 0.0 | 0.0 |
| Propylene + propane | 0.0 | 0.0 | 0.0 | 0.6 | 2.4 | 4.0 |
| Butanes | 0.0 | 0.0 | 0.0 | 0.0 | 0.9 | 1.1 |
| Butenes | 0.0 | 0.0 | 0.0 | 0.0 | 2.6 | 4.8 |
| Pentanes | 0.0 | 0.0 | 0.0 | 0.0 | 0.5 | 0.6 |
| Pentenes | 0.0 | 0.0 | 0.0 | 0.0 | 0.8 | 1.2 |
| C5+ | 0.0 | 0.0 | 0.0 | 0.0 | 0.9 | 2.5 |
| % iso in C4 | 0.0 | 0.0 | 0.0 | 0.0 | 70.2 | 71.0 |
| % C5+ aromatics | 0.0 | 0.0 | 0.0 | 0.0 | 59.3 | 87.2 |

Compared to the tables of examples 2 and 4, this table 3 shows a remarkable selectivity (99.4% by weight) of the catalyst in respect of the formation of ethylene and a quantitative (100%) conversion rate of the ethanol, when the reaction takes place at a temperature of 519 K.

EXAMPLE 7

Preparation of H-ZSM-5 catalyst having a ratio (M1−M2/n)/(Si+M1) of 0.01%

This catalyst was prepared under the same operating conditions as in example 1, except that the aluminium content was changed, by adjusting the amount of sodium aluminate in the reaction mixture.

The synthesis mixture had the following molar composition: 0.5 ($R_2O$); 5 ($NA_2O$); 0.012 ($Al_2O_3$); 24 ($SiO_2$) 1000 ($H_2O$) where R represents the tetrapropylammonium cation.

The calcination and ion exchange were carried out as described in example 1.

The X-ray diffraction analysis has shown the presence of a strongly crystalline phase of ZSM-5.

The obtained H-ZSM-5 catalyst did not contain sodium (M2) and had a ratio (M1)/(Si+M1) of 0.1%, M1 being aluminium. The size of the crystals was of 3 to 5 microns.

EXAMPLE 8

Conversion of ethanol into ethylene by means of the catalyst of example 7

An aqueous solution containing 90% by weight of ethanol has been reacted in contact with a sample of a catalyst of example 7, under the same reaction conditions as in example 2.

The operating conditions and analysis of the products are given in the following table 4.

TABLE 4

CATALYST: H—ZSM-5 (Al/Si + Al % = 0.1)

| REACTION CONDITIONS | | | | | | |
|---|---|---|---|---|---|---|
| Temperature (K) | 439 | 473 | 490 | 503 | 551 | 566 |
| LHSV (1/hr) | 0.31 | 0.31 | 0.31 | 0.31 | 0.31 | 0.31 |
| Conversion (%) | 13.0 | 33.3 | 62.0 | 96.1 | 100.0 | 100.0 |
| DISTRIBUTION OF THE PRODUCTS (% by weight) | | | | | | |
| Diethylether | 79.0 | 59.4 | 13.5 | 0.1 | 0.0 | 0.0 |
| Water | 19.1 | 24.2 | 35.6 | 38.9 | 39.0 | 39.0 |
| Hydrocarbons | 0.8 | 15.8 | 50.6 | 60.8 | 60.8 | 60.8 |
| CO | 1.1 | 0.6 | 0.3 | 0.2 | 0.2 | 0.2 |
| $CO_2$ | 0.0 | 0.0 | 0.0 | 0.0 | 0.0 | 0.0 |
| DISTRIBUTION OF THE HYDROCARBONS (% by weight) | | | | | | |
| Methane | 0.0 | 0.0 | 0.0 | 0.0 | 0.0 | 0.0 |
| Ethylene | 50.8 | 94.0 | 98.0 | 99.6 | 99.5 | 97.2 |
| Ethane | 0.0 | 0.0 | 0.0 | 0.0 | 0.0 | 0.0 |
| Propylene + propane | 0.0 | 0.0 | 0.0 | 0.0 | 0.0 | 0.0 |
| Butanes | 0.0 | 0.0 | 1.4 | 0.0 | 0.0 | 0.0 |
| Butenes | 49.2 | 6.0 | 0.6 | 0.4 | 0.0 | 0.2 |
| Pentanes | 0.0 | 0.0 | 0.0 | 0.0 | 0.0 | 0.0 |
| Pentenes | 0.0 | 0.0 | 0.0 | 0.0 | 0.0 | 0.0 |
| C5+ | 0.0 | 0.0 | 0.0 | 0.0 | 0.5 | 2.6 |
| % iso in $C_4$ | 0.0 | 0.0 | 69.1 | 0.0 | 0.0 | 0.0 |
| % $C_5+$ aromatics | 0.0 | 0.0 | 0.0 | 0.0 | 100.0 | 100.0 |

This table 4 shows a remarkable selectivity (99.5% by weight) for the formation of ethylene and at the same time a quantitative conversion rate (100%) at a reaction temperature of 551 K.

EXAMPLE 9

Preparation of a H-ZSM-5 catalyst having a ratio (M1−M2/n)/(Si+M1) of 1%

This catalyst has been prepared in the manner described in example 3, except that its aluminium content has been adapted by adding the adjusted amount of aluminium nitrate ($Al(NO_3)_3 9H_2O$) to constant amounts of $SiO_2$, NaOH and TPABr.

The synthesis mixture of the ZSM-5 zeolite had the following composition: 1000 $SiO_2$/Al $(NO_3)_3$; 13 NaOH; 83 TPABr; 13 $NH_4OH$; 662 $C_3H_5(OH)_3$.

The X-ray diffraction analysis has shown that the product consisted of 100% ZSM-5.

The solid product has been calcined and the H form of the zeolite has been obtained by ion exchange with HCl, as described in example 1.

EXAMPLE 10

Conversion of ethanol into ethylene by means of the catalyst of example 9

A diluted aqueous solution of ethanol, i.e. an aqueous solution containing 8.08% by weight (10% by volume) of ethanol has been contacted, in gaseous phase, with a sample of the catalyst of example 9, in the manner described in example 2, except that the flow rate of the ethanolic solution and the contact time of this solution with the catalyst have been changed as follows:

LHSV: 1.8 hours$^{-1}$.
Contact time: 0.16 second.

Two moles of helium per mole of ethanol have been used as diluent.

The results obtained at various temperatures are shown in the following table 5.

TABLE 5

CATALYST: H—ZSM-5 (Al/Si + Al % = 0.1)

| REACTION CONDITIONS | | | | | | |
|---|---|---|---|---|---|---|
| Temperature (K) | 497 | 581 | 603 | 654 | 665 | 685 |
| LHSV (1/hr) | 1.8 | 1.8 | 1.8 | 1.8 | 1.8 | 1.8 |
| Conversion (%) | 2.9 | 48.3 | 65.2 | 79.7 | 83.8 | 100.0 |
| DISTRIBUTION OF THE PRODUCTS (% by weight) | | | | | | |
| Diethylether | 79.8 | 25.3 | 13.6 | 2.5 | 0.9 | 0.0 |
| Water | 19.7 | 33.0 | 35.8 | 38.5 | 38.9 | 39.1 |
| Hydrocarbons | 0.5 | 41.7 | 50.6 | 59.0 | 60.2 | 60.9 |
| CO | 0.0 | 0.0 | 0.0 | 0.0 | 0.0 | 0.0 |
| $CO_2$ | 0.0 | 0.0 | 0.0 | 0.0 | 0.0 | 0.0 |
| DISTRIBUTION OF THE HYDROCARBONS (% by weight) | | | | | | |
| Methane | 0.0 | 0.0 | 0.0 | 0.0 | 0.0 | 0.0 |
| Ethylene | 100.0 | 100.0 | 100.0 | 100.0 | 100.0 | 100.0 |
| Ethane | 0.0 | 0.0 | 0.0 | 0.0 | 0.0 | 0.0 |
| Propylene + propane | 0.0 | 0.0 | 0.0 | 0.0 | 0.0 | 0.4 |
| Butanes | 0.0 | 0.0 | 0.0 | 0.0 | 0.0 | 0.0 |
| Butenes | 0.0 | 0.0 | 0.0 | 0.0 | 0.0 | 0.0 |
| Pentanes | 0.0 | 0.0 | 0.0 | 0.0 | 0.0 | 0.0 |
| Pentenes | 0.0 | 0.0 | 0.0 | 0.0 | 0.0 | 0.0 |
| C5+ | 0.0 | 0.0 | 0.0 | 0.0 | 0.0 | 0.0 |
| % iso in $C_4$ | 0.0 | 0.0 | 0.0 | 0.0 | 0.0 | 0.0 |
| % $C_5+$ aromatics | 0.0 | 0.0 | 0.0 | 0.0 | 0.0 | 0.0 |

This table shows that 8.08% by weight of ethanol in water have been quantitatively converted into ethylene with an ethylene carbon selectivity of 99.6% by weight at a temperature of 685 K.

EXAMPLE 11

Stability Test of a H-ZMS-5 catalyst having a ratio (M1−M2/n)/(Si+M1) of 0.1%

The H-ZSM-5 catalyst having an optimum molar proportion of aluminium (Al/Si+Al=0.1%) of example 7 has been submitted to a time on stream test under the same operating conditions as in example 2, except that the reaction temperature has been maintained at 553 K.

The liquid hourly space velocity of the starting ethanol-containing solution was of 0.31 hour$^{-1}$, said solution containing 90% by weight of ethanol.

This solution was contacted with the catalyst in gaseous phase.

The results obtained in this test are shown in the following table 6.

TABLE 6

CATALYST: H-ZSM-5 (0.1% Al/Si + Al)
REAGENT: 90% by weight of EtOH* in $H_2O$

| $\frac{g\ reagent}{g\ catalyst}$ | conversion** (%) | $C_2H_4$*** (% by weight) |
|---|---|---|
| 150 g/g | 100.0 | 99.5 |
| 300 g/g | 100.0 | 99.6 |
| 500 g/g | 100.0 | 99.7 |

TABLE 6-continued

| 800 g/g | 100.0 | 99.7 |
|---|---|---|

*EtOH = ethanol

**Conversion of EtOH (%) = $\frac{\text{amount (g) of converted EtOH}}{\text{amount (g) of supplied EtOH}} \times 100$

***Ethylene carbon selectivity (% by weight) =
$\frac{\text{amount (g) of formed } C_2H_4}{\text{amount (g) of formed hydrocarbons}} \times 100$ Table 6 shows that the conversion rate of ethanol into ethylene and the carbon selectivity for ethylene of the zeolite catalyst H-ZSM-5 containing 0.1% of Al/Si+Al do not change with the time.

Said table 6 shows also that the H-ZSM-5 catalyst having a ratio (M1)/(Si+M1), where M1 is aluminium, of 0.1% is remarkably stable for producing ethylene from ethanol in the presence of water.

EXAMPLE 12

Preparation of a catalyst of the silicalite type having a ratio (M1−M2/n)/(Si+M1) of 0.02%

This zeolite catalyst free from added aluminium has been synthesized by the procedure described in example 1 of U.S. Pat. No. 4,061,724.

Since this catalyst does not contain sodium (M2), the molar ratio (M1)/(Si+M1), where M1 is aluminium, is equal to 0.02%.

EXAMPLE 13

Conversion of ethanol into ethylene by means of the catalyst of example 12

An aqueous solution containing 90% by weight of ethanol has been passed over the catalyst of example 12 under the conditions of example 2.

The results of this test are shown in the following table 7.

TABLE 7

CATALYST: H—ZSM-5 (Al/Si + Al % = 0.02)

| REACTION CONDITIONS | | | | | | |
|---|---|---|---|---|---|---|
| Temperature (K) | 561 | 628 | 651 | 660 | 675 | 708 |
| LHSV (1/hr) | 0.31 | 0.31 | 0.31 | 0.31 | 0.31 | 0.31 |
| Conversion (%) | 1.6 | 10.1 | 35.0 | 94.7 | 99.8 | 100.0 |
| DISTRIBUTION OF THE PRODUCTS (% by weight) | | | | | | |
| Diethylether | 52.3 | 15.8 | 3.1 | 0.5 | 0.0 | 0.0 |
| Acetaldehyde | 11.1 | 13.8 | 6.4 | 2.7 | 0.9 | 4.6 |
| Water | 13.2 | 24.6 | 32.8 | 35.8 | 38.0 | 33.0 |
| Hydrocarbons | 12.1 | 40.1 | 54.7 | 58.8 | 60.3 | 58.3 |
| CO | 11.3 | 3.5 | 1.2 | 0.8 | 0.5 | 1.1 |
| CO2 | 0.0 | 2.2 | 1.8 | 1.4 | 0.3 | 3.0 |
| DISTRIBUTION OF THE HYDROCARBONS (% by weight) | | | | | | |
| Methane | 0.0 | 0.0 | 0.0 | 0.0 | 0.0 | 0.2 |
| Ethylene | 100.0 | 100.0 | 99.2 | 99.3 | 99.8 | 98.3 |
| Ethane | 0.0 | 0.0 | 0.0 | 0.0 | 0.0 | 0.0 |
| Propylene + propane | 0.0 | 0.0 | 0.0 | 0.0 | 0.0 | 1.2 |
| Butanes | 0.0 | 0.0 | 0.0 | 0.0 | 0.0 | 0.0 |
| Butenes | 0.0 | 0.0 | 0.8 | 0.7 | 0.2 | 0.3 |
| Pentanes | 0.0 | 0.0 | 0.0 | 0.0 | 0.0 | 0.0 |
| Pentenes | 0.0 | 0.0 | 0.0 | 0.0 | 0.0 | 0.0 |
| C5+ | 0.0 | 0.0 | 0.0 | 0.0 | 0.0 | 0.0 |
| % iso in C4 | 0.0 | 0.0 | 100.0 | 100.0 | 100.0 | 100.0 |
| % C5+ aromatics | 0.0 | 0.0 | 0.0 | 0.0 | 0.0 | 0.0 |

Table 7 shows that a conversion rate of almost 100% of ethanol is obtained at temperatures from 675 K. At this temperature, the selectivity of the zeolite catalyst for the formation of ethylene is maximum (99.8% by weight).

EXAMPLE 14

Stability test of a H-ZSM-5 catalyst having a ratio (M1−M2/n)/(Si+M1) of 0.1% in the conversion of an ethanolic product consisting of a fermentation liquor The H-ZSM-5 catalyst having an optimum aluminium molar proportion (Al/Si+Al=0.1%) of example 9 has been submitted to a life test.

A sample of the catalyst has been charged to a continuous flow tubular reactor adapted for a continuous flow and has been used without pretreatment.

An aqueous ethanolic solution derived from a fermentation liquid of the following composition has been used in gaseous phase:

8% by volume of ethanol with
0.2 ppm of acetaldehyde,
5.0 ppm of methanol,
0.3 ppm of n-propanol,
0.1 ppm of isobutanol,
0.1 ppm of n-butanol,
0.1 ppm of isoamyl alcohol and
0.2 ppm of acetone.

The reaction temperature has been maintained constant at 580 K

The liquid hourly space velocity (LHSV) of ethanol was of 0.25 hour$^{-1}$. Two moles of dry helium per mole of ethanol have been added as diluent.

The results of the analysis are given in table 8.

TABLE 8

CATALYST: H-ZSM-5 (0.1% Al/Si + Al)
REAGENT: 8% by weight of EtOH + impurities $\frac{\text{g reagent}}{\text{g catalyst}}$ :

| | conversion (%) | C2H4* (% by weight) |
|---|---|---|
| 0.1 g/g | 98 | 99.4 |
| 10.0 g/g | 98 | 99.5 |
| 50.0 g/g | 98 | 99.5 |
| 100.0 g/g | 98 | 99.5 |

*EtOH = ethanol

**Conversion of EtOH (%) = $\frac{\text{amount (g) of converted EtOH}}{\text{amount (g) of supplied EtOH}} \times 100$

***Ethylene carbon selectivity (% by weight) =
$\frac{\text{amount (g) of formed } C_2H_4}{\text{amount (g) of formed hydrocarbons}} \times 100$ Table 8 shows that the H-ZSM-5 catalyst containing 0.1% of Al/Si+Al has a high selectivity for the selective production of ethylene from an ethanol-containing fermentation liquor filtered on active coal.

The conversion rate of ethanol into ethylene and the ethylene carbon selectivity of the catalyst did not change during the duration of the test.

EXAMPLE 15

Preparation of a H-ZSM-5 catalyst having a ratio (M1−M2/n)/(Si+M1) of 0.33%

This catalyst has been prepared in the manner described in example 1, except that an adjusted amount of sodium borate (NaBO2) has been added to the reaction mixture instead of sodium aluminate (NaAlO2).

The molar composition of the synthesis mixture was as follows: 0.5 (R2O); 5 (Na2O); 0,12 (B2O3); 24 (SiO2);1000 (H2O), R representing the tetrapropylammonium cation.

The obtained solid product has been calcined at 873 K during 12 hours in the presence of air.

The ion exchange has been effected by refluxing the catalyst in an excess of ammonium chloride as described in example 5.

Prior to its use as catalyst, the zeolite has been activated in the reactor itself at 673 K under an atmosphere of helium during 1 hour.

After the synthesis and the pretreatment, the NMR analysis has shown that the boron content of the zeolite anionic structure is of 0.33% (M1)/(Si+Mi) where M1 is boron, the catalyst being free from sodium.

EXAMPLE 16

Conversion of ethanol into ethylene by means of the catalyst of example 15

After the above described treatment, an aqueous solution containing 90% by weight of ethanol has been passed over a sample of the catalyst of example 15.

The reaction conditions were the same as in example 2.

The results obtained at various temperatures are shown in the following table 9.

TABLE 9

CATALYST: H—ZSM-5 (B/Si + B % = 0.33)

| REACTION CONDITIONS | | | | | | |
|---|---|---|---|---|---|---|
| Temperature (K) | 436 | 481 | 507 | 530 | 553 | 600 |
| LHSV (1/hr) | 0.31 | 0.31 | 0.31 | 0.31 | 0.31 | 0.31 |
| Conversion (%) | 3.8 | 15.9 | 26.5 | 43.8 | 97.6 | 100.0 |
| DISTRIBUTION OF THE PRODUCTS (% by weight) | | | | | | |
| Diethylether | 80.4 | 78.6 | 69.5 | 45.8 | 0.0 | 0.0 |
| Water | 19.6 | 20.0 | 22.2 | 28.0 | 39.1 | 39.1 |
| Hydrocarbons | 0.0 | 1.4 | 8.3 | 26.2 | 60.9 | 60.9 |
| CO | 0.0 | 0.0 | 0.0 | 0.0 | 0.0 | 0.0 |
| $CO_2$ | 0.0 | 0.0 | 0.0 | 0.0 | 0.0 | 0.0 |
| DISTRIBUTION OF THE HYDROCARBONS (% by weight) | | | | | | |
| Methane | 0.0 | 0.0 | 0.0 | 0.0 | 0.0 | 0.0 |
| Ethylene | 0.0 | 100.0 | 94.9 | 98.4 | 99.0 | 95.4 |
| Ethane | 0.0 | 0.0 | 0.0 | 0.0 | 0.0 | 0.1 |
| Propylene + propane | 0.0 | 0.0 | 0.3 | 0.1 | 0.5 | 0.6 |
| Butanes | 0.0 | 0.0 | 0.0 | 0.0 | 0.0 | 0.0 |
| Butenes | 0.0 | 0.0 | 4.8 | 1.5 | 0.5 | 0.3 |
| Pentanes | 0.0 | 0.0 | 0.0 | 0.0 | 0.0 | 0.0 |
| Pentenes | 0.0 | 0.0 | 0.0 | 0.0 | 0.0 | 0.0 |
| $C_5+$ | 0.0 | 0.0 | 0.0 | 0.0 | 0.0 | 3.6 |
| % iso in $C_4$ | 0.0 | 0.0 | 23.9 | 18.3 | 15.7 | 16.3 |
| % $C_5+$ aromatics | 0.0 | 0.0 | 0.0 | 0.0 | 0.0 | 23.0 |

This table 9 shows an ethylene carbon selectivity of 99 by weight and a conversion rate of ethanol of about 100%, when the reaction is carried out at 553 K.

EXAMPLE 17

Preparation of a Na-ZSM-5 catalyst having a ratio (M1−M2/n)/(Si+M1) of 0.33%

11.1 g of $SiO_2$ (aerosil) have been added to a solution of sodium hydroxide (1,6 g of NaOH in 32 ml of water), so as to obtain a solution 1.

This solution 1 has been mixed, while vigorously stirring, with a solution 2 consisting of 2.48 g of tetrapropylammonium bromide in 38 ml of water.

A third solution comprising 0.666 g of sodium aluminate dissolved in 10 ml of water has been added with continuous stirring to the obtained solution.

The pH of the mixture has then been adjusted to a value of 10 by means of concentrated sulfuric acid. Finally, 40 ml of water have been added.

The composition of the reaction mixture on a molar basis was as follows: 60 $SiO_2/Al_2O_3$; 4 NaOH; 6 TPABr; 666 $H_2O$.

The obtained gel has been crystallised in autoclaves under autogeneous pressure of the reaction mixture during 3 days, at a temperature of 423 K, the gel being stirred during said crystallisation.

The obtained solid product has been separated from the supernatant liquid by filtration, then washed with water, dried and calcined in the presence of air at a temperature of 823 K during 12 hours.

The X-ray analysis has shown that the product was 100% ZSM-5 zeolite.

The ion exchange with the sodium cation has been obtained by refluxing the catalyst in an excess of 0.5N sodium chloride during 4 hours.

The atomic absorption analysis has shown that a Na-ZSM-5 catalyst having a (M1−M2/n)/(Si+M1) ratio of 0.33% has been obtained.

EXAMPLE 18

Conversion of ethanol into ethylene by means of the catalyst of example 17

An aqueous solution of ethanol has been passed, in gaseous phase, on the catalyst of example 17 under the reaction conditions of example 2, except that the liquid hourly space velocity (LHSV) and the contact time of the reagent have been changed as follows:

LHSV: 0.37 hour$^{-1}$.

contact time: 0.9 second.

The operating conditions and results are given in the following table 10.

TABLE 10

CATALYST: Na—ZSM-5 ((M1 − M2/n)/(Si + M1) % = 0.33)

| REACTION CONDITIONS | | | | | |
|---|---|---|---|---|---|
| Temperature (K) | 554 | 575 | 593 | 616 | 635 |
| LHSV (1/hr) | 0.37 | 0.37 | 0.37 | 0.37 | 0.37 |
| Conversion (%) | 100.0 | 80.3 | 100.0 | 100.0 | 100.0 |
| DISTRIBUTION OF THE PRODUCTS (% by weight) | | | | | |
| Diethylether | 45.1 | 3.6 | 0.0 | 0.0 | 0.0 |
| Acetaldehyde | 0.0 | 0.0 | 0.0 | 0.0 | 0.8 |
| Water | 28.1 | 38.2 | 39.1 | 39.1 | 38.8 |
| Hydrocarbons | 26.8 | 58.2 | 60.9 | 60.9 | 60.4 |
| CO | 0.0 | 0.0 | 0.0 | 0.0 | 0.0 |
| $CO_2$ | 0.0 | 0.0 | 0.0 | 0.0 | 0.0 |
| DISTRIBUTION OF THE HYDROCARBONS (% by weight) | | | | | |
| Methane | 0.0 | 0.0 | 0.0 | 0.0 | 0.0 |
| Ethylene | 100.0 | 99.5 | 99.7 | 99.9 | 99.8 |
| Ethane | 0.0 | 0.0 | 0.0 | 0.0 | 0.0 |
| Propylene + propane | 0.0 | 0.0 | 0.0 | 0.1 | 0.2 |
| Butanes | 0.0 | 0.0 | 0.0 | 0.0 | 0.0 |
| Butenes | 0.0 | 0.5 | 0.3 | 0.0 | 0.0 |
| Pentanes | 0.0 | 0.0 | 0.0 | 0.0 | 0.0 |
| Pentenes | 0.0 | 0.0 | 0.0 | 0.0 | 0.0 |
| $C_5+$ | 0.0 | 0.0 | 0.0 | 0.0 | 0.0 |
| % iso in $C_4$ | 0.0 | 0.0 | 0.0 | 0.0 | 0.0 |
| % $C_5+$ aromatics | 0.0 | 0.0 | 0.0 | 0.0 | 0.0 |

This table shows a remarkable selectivity (at least 99.7% by weight) of the catalyst for the formation of ethylene and a conversion rate of 100% from a reaction temperature of 593 K.

EXAMPLE 19

Preparation of a Na-ZSM-5 catalyst having a molar ratio (M1−M2/n)/(Si+M1) of 0.05%

This catalyst has been synthesized in the manner described in example 17.

The ion exchange with the sodium cation has been carried out as described in example 17.

The atomic absorption analysis has shown that the obtained catalyst had a (M1−M2/n)/(Si+M1) ratio of 0.05%.

EXAMPLE 20

Conversion of ethanol into ethylene by means of the catalyst of example 19

The reaction conditions of example 2 have been applied except that the liquid hourly space velocity (LHSV) and the contact time of the reagent with the catalyst have been changed as follows:
LHSV: $0.10^{-1}$.
Contact time: 0.9 second.

The following table 11 shows the results of this test.

TABLE 11

CATALYST: Na—ZSM-5 ((M1 − M2/n)/(Si + M1) % = 0.05)

| REACTION CONDITIONS | | | | | | |
|---|---|---|---|---|---|---|
| Temperature (K) | 629 | 642 | 652 | 662 | 668 | 707 |
| LHSV (1/hr) | 0.10 | 0.10 | 0.10 | 0.10 | 0.10 | 0.10 |
| Conversion (%) | 77.7 | 92.9 | 97.3 | 100.0 | 100.0 | 100.0 |
| DISTRIBUTION OF THE PRODUCTS (% by weight) | | | | | | |
| Diethylether | 0.4 | 0.0 | 0.0 | 0.0 | 0.0 | 0.0 |
| Acetaldehyde | 0.0 | 0.0 | 0.0 | 0.0 | 0.0 | 2.6 |
| Water | 39.0 | 39.1 | 39.1 | 39.1 | 39.1 | 38.1 |
| Hydrocarbons | 60.6 | 60.9 | 60.9 | 60.9 | 60.9 | 59.3 |
| CO | 0.0 | 0.0 | 0.0 | 0.0 | 0.0 | 0.0 |
| CO₂ | 0.0 | 0.0 | 0.0 | 0.0 | 0.0 | 0.0 |
| DISTRIBUTION OF THE HYDROCARBONS (% by weight) | | | | | | |
| Methane | 0.0 | 0.0 | 0.0 | 0.0 | 0.0 | 0.0 |
| Ethylene | 99.4 | 99.7 | 99.7 | 99.7 | 99.7 | 99.6 |
| Ethane | 0.0 | 0.0 | 0.0 | 0.0 | 0.0 | 0.0 |
| Propylene + propane | 0.3 | 0.3 | 0.3 | 0.3 | 0.3 | 0.4 |
| Butanes | 0.0 | 0.0 | 0.0 | 0.0 | 0.0 | 0.0 |
| Butenes | 0.3 | 0.0 | 0.0 | 0.0 | 0.0 | 0.0 |
| Pentanes | 0.0 | 0.0 | 0.0 | 0.0 | 0.0 | 0.0 |
| Pentenes | 0.0 | 0.0 | 0.0 | 0.0 | 0.0 | 0.0 |
| C5+ | 0.0 | 0.0 | 0.0 | 0.0 | 0.0 | 0.0 |
| % iso in C4 | 0.0 | 0.0 | 0.0 | 0.0 | 0.0 | 0.0 |
| % C5+ aromatics | 0.0 | 0.0 | 0.0 | 0.0 | 0.0 | 0.0 |

This table 11 shows that a quantitative conversion rate as well as an ethylene carbon selectivity at least equal to 99% by weight have been obtained from a temperature of 662 K in the reaction conditions in question.

EXAMPLE 21

Preparation of a Ca-ZSM-5 catalyst having a molar ratio (M1−M2/n)/(Si+M1) of 0.24%

This catalyst has been synthesized under the same operating conditions as in example 1, except that the aluminium content has been modified by changing the amount of sodium aluminate (NaAlO₂) and that an adjusted amount of tetrapropylammonium bromide (TPABr: 2.84 g) has been used instead of the hydroxide.

The molar composition of the synthesis mixture was as follows: 0.5 (R₂O); 5 (Na₂O); 0.4 (Al₂O₃); 24 (SiO₂);1000 (H₂O) R representing the tetra-propylammonium organic cation.

The X-ray diffraction analysis has shown that the product was 100% of ZSM-5.

The ion exchange with the calcium cation was obtained by refluxing the zeolite with an excess of 0.5N calcium chloride during 4 hours.

The atomic absorption analysis has shown that the molar ratio (M1−M2/n)/(Si+M1) of the Ca-ZSM-5 catalyst was of 0.24%. The crystals of the catalyst had a size of about 4 microns.

EXAMPLE 22

Conversion of ethanol into ethylene by means of the catalyst of example 21

The operating conditions were the same as in example 2, except that the LHSV and the contact time of the reagent have been changed as follows:
LHSV: $0.1$ hour$^{-1}$.
Contact time: 0.9 second.

The following table 12 shows the operating conditions and the products obtained at various reaction temperatures.

TABLE 12

CATALYST: Ca—ZSM-5 ((M1 − M2/n)/(Si + M1) % = 0.24)

| REACTION CONDITIONS | | | | | |
|---|---|---|---|---|---|
| Temperature (K) | 514, | 530, | 543, | 572, | 594, |
| LHSV (1/hr) | 0.10 | 0.10 | 0.10 | 0.10 | 0.10 |
| Conversion (%) | 49.6 | 77.1 | 100.0 | 100.0 | 100.0 |
| DISTRIBUTION OF PRODUCTS (% by weight) | | | | | |
| Diethylether | 53.0 | 7.0 | 0.0 | 0.0 | 0.0 |
| Acetaldehyde | 0.0 | 0.0 | 0.0 | 0.0 | 0.0 |
| Water | 26.2 | 37.4 | 39.1 | 39.1 | 39.1 |
| Hydrocarbons | 20.8 | 55.6 | 60.9 | 60.9 | 60.9 |
| CO | 0.0 | 0.0 | 0.0 | 0.0 | 0.0 |
| CO₂ | 0.0 | 0.0 | 0.0 | 0.0 | 0.0 |
| DISTRIBUTION OF THE HYDROCARBONS (% by weight) | | | | | |
| Methane | 0.0 | 0.0 | 0.0 | 0.0 | 0.0 |
| Ethylene | 100.0 | 99.8 | 99.7 | 99.8 | 99.7 |
| Ethane | 0.0 | 0.0 | 0.0 | 0.0 | 0.0 |
| Propylene + Propane | 0.0 | 0.0 | 0.1 | 0.2 | 0.3 |
| Butanes | 0.0 | 0.0 | 0.0 | 0.0 | 0.0 |
| Butenes | 0.0 | 0.2 | 0.2 | 0.0 | 0.0 |
| Pentanes | 0.0 | 0.0 | 0.0 | 0.0 | 0.0 |
| Pentenes | 0.0 | 0.0 | 0.0 | 0.0 | 0.0 |
| C5+ | 0.0 | 0.0 | 0.0 | 0.0 | 0.0 |
| % iso in C4 | 0.0 | 0.0 | 0.0 | 0.0 | 0.0 |
| % C5+ aromatics | 0.0 | 0.0 | 0.0 | 0.0 | 0.0 |

A conversion rate of 100% and an ethylene carbon selectivity of more than 99% by weight have been obtained from a temperature of 543 K.

EXAMPLE 23

Preparation of a H-ZSM-5 catalyst having a Al/Si+Al of 1.5% after a hydrothermal treatment by means of water vapor

The catalyst was prepared as described in example 17.

On a molar basis, the synthesis mixture of the ZSM-5 zeolite had the following composition: 60 SiO₂/Al₂O₃; 4 NaOH; 6 TPABr; 666 H₂O.

After the synthesis, the solid product has been activated by removing the TPA organic cation by calcination in the presence of air at 832 K during 12 hours.

The catalyst was pretreated by means of water vapor at a temperature of 973 K during 24 hours, so as to decrease the (M1−M2/n)/(Si+M1) ratio which was of 2.70%, by partial removal of aluminium from the rigid tridimensional framework.

The flow rate (LHSV) of water vapor on the catalyst was of 0.8 hour$^{-1}$. The ion exchange with the ammonium cation was obtained by refluxing the zeolite with an excess of 0.5N ammonium chloride during 4 hours.

The hydrogen form was obtained by calcining the catalyst in the reactor itself at a temperature of 673 K under a stream of helium during 1 hour.

According to the results of atomic absorption analysis after the extraction of the aluminium in the cationic positions and according to the NMR analysis, a H-ZSM-5 catalyst containing 1.50% of Al/Si+Al, in which Al is framework aluminium, i.e. Al bound by tetraedric coordination, has been obtained.

The aluminium which was not bound by tetraedric coordination has been washed out with NaOH as described by Kerr (J. Catalysis, 15, 200 (1969)).

EXAMPLE 24

Conversion of ethanol into ethylene by means of the catalyst of example 23

A sample of the catalyst of example 23 was placed in a tubular reactor. The same reaction conditions as in example 2 have been used, except in respect of the liquid hourly space velocity (LHSV) of ethanol and in respect of the contact time of the ethanol with the catalyst, which were as follows:

LHSV: 0.1 hour$^{-1}$.

Contact time: 0.9 second.

Table 13 shows the operating conditions and the results.

TABLE 13

CATALYST: H—ZSM-5 (Al/Si + Al % = 1.5)

| REACTION CONDITIONS | | | | | | |
|---|---|---|---|---|---|---|
| Temperature (K) | 490, | 500, | 510, | 529, | 550, | 576, |
| LHSV (1/hr) | 0.10 | 0.10 | 0.10 | 0.10 | 0.10 | 0.10 |
| Conversion (%) | 60.8 | 77.4 | 100.0 | 100.0 | 100.0 | 100.0 |
| DISTRIBUTION OF PRODUCTS (% by weight) | | | | | | |
| Diethylether | 37.1 | 10.9 | 0.0 | 0.0 | 0.0 | 0.0 |
| Acetaldehyde | 0.0 | 0.0 | 0.0 | 0.0 | 0.0 | 0.0 |
| Water | 30.1 | 36.5 | 39.1 | 39.1 | 39.1 | 39.1 |
| Hydrocarbons | 32.8 | 52.6 | 60.9 | 60.9 | 60.9 | 60.9 |
| CO | 0.0 | 0.0 | 0.0 | 0.0 | 0.0 | 0.0 |
| CO$_2$ | 0.0 | 0.0 | 0.0 | 0.0 | 0.0 | 0.0 |
| DISTRIBUTION OF THE HYDROCARBONS (% by weight) | | | | | | |
| Methane | 0.0 | 0.0 | 0.0 | 0.0 | 0.0 | 0.0 |
| Ethylene | 100.0 | 100.0 | 99.7 | 99.4 | 99.7 | 99.8 |
| Ethane | 0.0 | 0.0 | 0.0 | 0.0 | 0.0 | 0.0 |
| Propylene + Propane | 0.0 | 0.0 | 0.3 | 0.6 | 0.3 | 0.2 |
| Butanes | 0.0 | 0.0 | 0.0 | 0.0 | 0.0 | 0.0 |
| Butenes | 0.0 | 0.0 | 0.0 | 0.0 | 0.0 | 0.0 |
| Pentanes | 0.0 | 0.0 | 0.0 | 0.0 | 0.0 | 0.0 |
| Pentenes | 0.0 | 0.0 | 0.0 | 0.0 | 0.0 | 0.0 |
| C5+ | 0.0 | 0.0 | 0.0 | 0.0 | 0.0 | 0.0 |
| % iso in C$_4$ | 0.0 | 0.0 | 0.0 | 0.0 | 0.0 | 0.0 |
| % C$_5$+ aromatics | 0.0 | 0.0 | 0.0 | 0.0 | 0.0 | 0.0 |

When the H-ZSM-5 zeolite catalyst treated with water vapor is used, it is possible to obtain at a flow rate of 0.1 hour$^{-1}$ of ethanol of a liquor containing 90% by weight of ethanol, a conversion rate of ethanol of 100% and an ethylene carbon selectivity of 99.7% by weight, when the catalyst is maintained at a temperature of 510 K.

As shown in example 26, it is not possible to reach a conversion rate of 100% as well as an ethylene carbon selectivity of at least 99% by weight when the same starting H-ZSM-5 catalyst having a molar ratio Al/Si+Al of 2.70% is used.

EXAMPLE 25

Preparation of a H-ZSM-5 catalyst having a molar ratio Al/Si+Al of 2.70%

This catalyst was prepared in the manner described in example 17.

The molar composition of the synthesis mixture of the ZSM-5 zeolite catalyst was as follows: 60 SiO$_2$/Al$_2$O$_3$; 4 NaOH; 6 TPABr; 666 H$_2$O.

The solid product was activated by removing the organic TPA cation in the presence of air at 823 K during 12 hours.

The X-ray analysis has shown that the product was 100% ZSM-5 zeolite.

The hydrogen form of the zeolite was obtained by ion exchange as described in example 23.

A H-ZSM-5 catalyst having a Al/Si+Al ratio of 2.70% has been obtained with a crystal size of about 4 microns.

EXAMPLE 26

Conversion of ethanol into ethylene by means of the catalyst of example 25

This test has been carried out as described in example 2, except that the LHSV and the contact time have been modified, in order to try to obtain optimum conditions for reaching a conversion rate of ethanol of 100% and an ethylene carbon selectivity at least equal to about 99% by weight.

The following table 14 shows the optimum reaction conditions and the results.

TABLE 14

CATALYST: H—ZSM-5 (Al/Si + Al % = 2.70)

| REACTION CONDITIONS | | | | | | |
|---|---|---|---|---|---|---|
| Temperature (K) | 437, | 476, | 488, | 499, | 522, | 560, |
| LHSV (1/hr) | 0.18 | 0.18 | 0.18 | 0.18 | 0.18 | 0.18 |
| Conversion (%) | 38.1 | 99.2 | 100.0 | 100.0 | 100.0 | 100.0 |
| DISTRIBUTION OF PRODUCTS (% by weight) | | | | | | |
| Diethylether | 66.2 | 0.0 | 0.0 | 0.0 | 0.0 | 0.0 |
| Acetaldehyde | 0.0 | 0.6 | 0.0 | 0.0 | 0.0 | 0.0 |
| Water | 23.0 | 39.1 | 39.1 | 39.0 | 39.1 | 39.2 |
| Hydrocarbons | 10.8 | 60.9 | 60.9 | 61.0 | 60.9 | 60.8 |
| CO | 0.0 | 0.0 | 0.0 | 0.0 | 0.0 | 0.0 |
| CO$_2$ | 0.0 | 0.0 | 0.0 | 0.0 | 0.0 | 0.0 |
| DISTRIBUTION OF THE HYDROCARBONS (% by weight) | | | | | | |
| Methane | 0.0 | 0.0 | 0.0 | 0.0 | 0.0 | 0.0 |
| Ethylene | 98.6 | 92.1 | 85.9 | 72.8 | 49.1 | 27.0 |
| Ethane | 0.0 | 0.0 | 0.2 | 0.0 | 0.2 | 0.3 |
| Propylene + Propane | 0.0 | 1.0 | 1.9 | 3.2 | 5.5 | 9.4 |
| Butanes | 0.0 | 0.4 | 1.5 | 2.4 | 2.9 | 8.0 |
| Butenes | 0.0 | 0.2 | 0.7 | 4.1 | 8.7 | 11.7 |
| Pentanes | 0.0 | 0.5 | 1.2 | 2.2 | 2.4 | 4.9 |
| Pentenes | 0.0 | 0.0 | 0.4 | 2.2 | 5.2 | 6.1 |
| C5+ | 1.4 | 5.8 | 8.2 | 13.1 | 26.0 | 32.6 |
| % iso in C$_4$ | 0.0 | 23.0 | 39.0 | 59.5 | 61.2 | 68.9 |
| % C$_5$+ aromatics | 0.0 | 0.0 | 8.4 | 10.0 | 35.4 | 59.6 |

This table shows that this catalyst which has a molar ratio Al/Si+Al (%) of more than the claimed maximum had such an aluminium content that its acidity is too high for catalysing selectively the dehydration of ethanol into ethylene, so as to obtain a quantitative conversion rate and an ethylene carbon selectivity of at least 99% by weight.

EXAMPLE 27

Preparation of a Ca-ZSM-5 catalyst having a molar ratio $(M1-M2/n)(Si+M1)$ of 1.65%

This catalyst was prepared as described in example 17. On a molar basis, the obtained gel had the following composition: 60 $SiO_2/Al_2O_3$; 4 NaOH; 6 TPABr; 666 $H_2O$.

The solid product obtained by hydrothermal crystallization has been calcined in the manner described in example 17.

The zeolite has then been submitted three times to an ion exchange by refluxing the catalyst in an excess of 0.5N calcium chloride during 4 hours.

The results of atomic absorption analysis have shown that the molar ratio $(M1-M2/n)/(Si+M1)$ of the Ca-ZSM-5 zeolite was equal to 1.65%.

EXAMPLE 28

Conversion of ethanol into ethylene by means of the catalyst of example 27

This test was carried out in the manner described in example 26.

The following table 15 shows the reactions conditions and the results:

TABLE 15

CATALYST: Ca—ZSM-5 $((M1 - M2/n)(Si + M1)$ % = 1.65)

| REACTION CONDITIONS | | | | | | |
|---|---|---|---|---|---|---|
| Temperature (K) | 489, | 511, | 523, | 543, | 573, | 613, |
| LHSV (1/hr) | 0.18 | 0.18 | 0.18 | 0.18 | 0.18 | 0.18 |
| Conversion (%) | 61.1 | 76.6 | 100.0 | 100.0 | 100.0 | 100.0 |
| DISTRIBUTION OF PRODUCTS (% by weight) | | | | | | |
| Diethylether | 51.8 | 13.7 | 0.0 | 0.0 | 0.0 | 0.0 |
| Acetaldehyde | 0.0 | 0.6 | 0.0 | 0.0 | 0.0 | 0.0 |
| Water | 26.5 | 35.5 | 39.0 | 39.1 | 39.2 | 39.2 |
| Hydrocarbons | 21.7 | 50.2 | 61.0 | 60.9 | 60.8 | 60.8 |
| CO | 0.0 | 0.0 | 0.0 | 0.0 | 0.0 | 0.0 |
| $CO_2$ | 0.0 | 0.0 | 0.0 | 0.0 | 0.0 | 0.0 |
| DISTRIBUTION OF THE HYDROCARBONS (% by weight) | | | | | | |
| Methane | 0.0 | 0.0 | 0.0 | 0.0 | 0.0 | 0.0 |
| Ethylene | 100.0 | 93.9 | 72.6 | 46.1 | 36.2 | 47.8 |
| Ethane | 0.0 | 0.0 | 0.8 | 0.4 | 0.4 | 0.0 |
| Propylene + Propane | 0.0 | 0.4 | 3.3 | 8.1 | 10.6 | 13.6 |
| Butanes | 0.0 | 0.1 | 3.5 | 5.9 | 6.9 | 4.3 |
| Butenes | 0.0 | 1.1 | 4.0 | 12.3 | 12.9 | 13.2 |
| Pentanes | 0.0 | 1.3 | 3.1 | 3.8 | 3.5 | 1.9 |
| Pentenes | 0.0 | 0.0 | 1.8 | 6.9 | 6.0 | 5.1 |
| C5+ | 0.0 | 3.2 | 10.9 | 16.5 | 23.5 | 14.1 |
| % iso in $C_4$ | 0.0 | 6.7 | 73.2 | 68.1 | 69.1 | 66.9 |
| % $C_5+$ aromatics | 0.0 | 0.0 | 0.0 | 35.8 | 67.7 | 69.4 |

It has to be noticed that the molar ratio $(M1-M2/n)/(Si+M1)$ in % is higher than the claimed maximum (1,5%) and that there are no operating conditions under which the conversion rate is of 100% and the ethylene carbon selectivity reaches more than 99% by weight.

EXAMPLE 29

Preparation of a La-ZSM-5 catalyst having a molar ratio $(M1-M2/n)/(Si+M1)$ of 1.75%

The catalyst was synthesized as described in example 17.

On a molar basis, the reaction mixture had the following composition: 60 $SiO_2/Al_2O_3$; 4 NaOH; 6 TPABr; 666 $H_2O$.

After crystallization the solid product was separated from the liquid solution, washed with water, dried and calcined in the presence of air.

An ion exchange was carried out three times by refluxing the catalyst in an excess of 0.1N lanthanum nitrate $(La(NO_3)_3)$ during 4 hours.

The molar ratio $(M1-M2/n)/(Si+M1)$ of the so obtained catalyst was of 1.75%.

EXAMPLE 30

Conversion of ethanol into ethylene by means of the catalyst of example 29

The operating conditions were the same as in example 26.

Table 16 summarizes the operating conditions and the results:

TABLE 16

CATALYST: La—ZSM-5 $((M1 - M2/n)(Si + M1)$ % = 1.75)

| REACTION CONDITIONS | | | | | | |
|---|---|---|---|---|---|---|
| Temperature (K) | 476, | 500, | 510, | 519, | 541, | 562, |
| LHSV (1/hr) | 0.18 | 0.18 | 0.18 | 0.18 | 0.18 | 0.18 |
| Conversion (%) | 60.2 | 76.4 | 100.0 | 100.0 | 100.0 | 100.0 |
| DISTRIBUTION OF PRODUCTS (% by weight) | | | | | | |
| Diethylether | 53.5 | 19.5 | 0.0 | 0.0 | 0.0 | 0.0 |
| Acetaldehyde | 0.0 | 0.5 | 0.0 | 0.0 | 0.0 | 0.0 |
| Water | 26.1 | 34.2 | 39.0 | 38.9 | 39.1 | 39.1 |
| Hydrocarbons | 20.4 | 45.8 | 61.0 | 61.1 | 60.9 | 60.9 |
| CO | 0.0 | 0.0 | 0.0 | 0.0 | 0.0 | 0.0 |
| $CO_2$ | 0.0 | 0.0 | 0.0 | 0.0 | 0.0 | 0.0 |
| DISTRIBUTION OF THE HYDROCARBONS (% by weight) | | | | | | |
| Methane | 0.0 | 0.0 | 0.0 | 0.0 | 0.0 | 0.0 |
| Ethylene | 100.0 | 96.1 | 86.4 | 57.1 | 38.6 | 29.9 |
| Ethane | 0.0 | 0.0 | 0.7 | 1.1 | 0.5 | 0.4 |
| Propylene + Propane | 0.0 | 0.4 | 2.3 | 4.9 | 8.7 | 10.8 |
| Butanes | 0.0 | 0.0 | 1.8 | 5.7 | 6.9 | 9.1 |
| Butenes | 0.0 | 1.3 | 1.3 | 6.9 | 13.2 | 12.9 |
| Pentanes | 0.0 | 0.2 | 1.8 | 4.7 | 4.7 | 5.0 |
| Pentenes | 0.0 | 0.0 | 0.2 | 3.8 | 7.6 | 6.7 |
| C5+ | 0.0 | 2.0 | 5.5 | 15.8 | 20.0 | 25.1 |
| % iso in $C_4$ | 0.0 | 0.0 | 63.5 | 70.4 | 66.8 | 72.1 |
| % $C_5+$ aromatics | 0.0 | 0.0 | 0.0 | 2.5 | 38.1 | 62.4 |

This catalyst which has a molar ratio $(M1-M2/n)/(Si+M1)$ of more than 1.5% has such an acidity that it does not selectively catalyse the dehydration of ethanol into ethylene. Indeed, a quantitative conversion rate and an ethylene carbon selectivity of at least 99% cannot be obtained with this catalyst.

EXAMPLE 31

Preparation of a H-ZMS-11 catalyst having a molar ratio $Al/Si+Al$ of 1.0%

This catalyst has been synthesized by using the same operating conditions as in example 1, except that its aluminium content has been adapted by adding an adjusted amount of sodium aluminate $(NaAlO_2)$ to the reaction medium and that the tetrapropylammonium hydroxide (TPAOH) was replaced by an adjusted amount of tetrabutylammonium hydroxide (TBAOH).

The synthesis mixture of the ZSM-11 zeolite had the following molar composition: $0.5(R_2O)$; $5(Na_2O)$; $0.12(Al_2O_3)$; $24(SiO_2)$; $1000(H_2O)$ where R represents the tetrabutylammonium cation.

The calcination and the ion exchange have been carried out as described in example 1.

The X-ray diffraction analysis has shown the presence of a strongly crystalline phase of ZSM-11.

The H-ZSM-11 catalyst had a molar ratio Al/Si+Al of 1.0% and the crystals of this catalyst had a size of about 4 microns.

EXAMPLE 32

Conversion of ethanol into ethylene by means of the catalyst of example 31

The same operating conditions as in example 2 have been used, except that the liquid hourly space velocity (LHSV) and the contact time of the reagent have been changed as follows:

LHSV: 0.15 hour$^{-1}$
Contact time: 0.9 second.

The result of this test and the operating conditions are summarized in the following table 17.

TABLE 17

CATALYST: H—ZSM-5 (Al/Si + Al % = 1.00)

| REACTION CONDITIONS | | | | | | |
|---|---|---|---|---|---|---|
| Temperature (K) | 510, | 520, | 529, | 551, | 581, | 606, |
| LHSV (1/hr) | 0.15 | 0.15 | 0.15 | 0.15 | 0.15 | 0.15 |
| Conversion (%) | 69.9 | 91.3 | 100.0 | 100.0 | 100.0 | 100.0 |
| DISTRIBUTION OF PRODUCTS (% by weight) | | | | | | |
| Diethylether | 16.0 | 1.8 | 0.0 | 0.0 | 0.0 | 0.0 |
| Acetaldehyde | 0.0 | 0.2 | 0.0 | 0.0 | 0.0 | 0.0 |
| Water | 35.2 | 38.6 | 39.1 | 39.1 | 39.1 | 39.1 |
| Hydrocarbons | 48.8 | 59.4 | 60.9 | 60.9 | 60.9 | 60.9 |
| CO | 0.0 | 0.0 | 0.0 | 0.0 | 0.0 | 0.0 |
| CO$_2$ | 0.0 | 0.0 | 0.0 | 0.0 | 0.0 | 0.0 |
| DISTRIBUTION OF THE HYDROCARBONS (% by weight) | | | | | | |
| Methane | 0.0 | 0.0 | 0.0 | 0.0 | 0.0 | 0.0 |
| Ethylene | 100.0 | 99.2 | 99.0 | 99.0 | 99.3 | 99.3 |
| Ethane | 0.0 | 0.0 | 0.0 | 0.0 | 0.0 | 0.0 |
| Propylene + Propane | 0.0 | 0.2 | 0.4 | 0.5 | 0.4 | 0.4 |
| Butanes | 0.0 | 0.1 | 0.1 | 0.1 | 0.0 | 0.0 |
| Butenes | 0.0 | 0.5 | 0.5 | 0.4 | 0.3 | 0.3 |
| Pentanes | 0.0 | 0.0 | 0.0 | 0.0 | 0.0 | 0.0 |
| Pentenes | 0.0 | 0.0 | 0.0 | 0.0 | 0.0 | 0.0 |
| C$_5$+ | 0.0 | 0.0 | 0.0 | 0.0 | 0.0 | 0.0 |
| % iso in C$_4$ | 0.0 | 12.1 | 21.5 | 20.9 | 13.9 | 8.7 |
| % C$_5$+ aromatics | 0.0 | 0.0 | 0.0 | 0.0 | 0.0 | 0.0 |

A carbon selectivity for ethylene of at least 99% by weight as well as a quantitative conversion rate have been obtained from a temperature of 529 K.

EXAMPLE 33

Preparation of a H-ZSM-48 catalyst having a molar ratio (M1−M2/n)/(Si+M1) of 0.24%

The following starting solutions have been used:
(a) 37.34 g of an aqueous solution of sodium silicate containing aluminium as impurity in 80 ml of water,
(b) 1.87 ml of concentrated sulfuric acid,
(c) 8.434 g of tetramethylammonium bromide (TMABr) and 36.2 g of octylamine in 80 ml of water.

The sulfuric acid (b) has been added to solution (a) under vigorous stirring (a).

On a molar basis, the obtained gel had the following composition: 600 SiO$_2$/Al$_2$O$_3$; 5 Na$_2$O; 5,5 TMABr; 27,5 octylamine; 1000 H$_2$O.

This gel has been stirred in autoclaves at a temperature of 433 K during 2 days. After washing, drying and calcination in the presence of air at a temperature of 823 K during 12 hours, the solid product has been submitted to a X-ray diffraction analysis. This analysis has shown the presence of a strongly crystaline phase of ZSM-48.

The hydrogen form of the catalyst has been obtained in the manner described in example 1.

The results of atomic absorption analysis have shown that the ratio (M1−M2/n)/(Si+M1) of the zeolite was of 0.24%.

EXAMPLE 34

Conversion of ethanol into ethylene by means of the catalyst of example 33

The reaction conditions of example 2 have been applied, except that the liquid hourly space velocity (LHSV) and the contact time of the catalyst have been changed as follows:

LHSV: 0.27 hour$^{-1}$.
Contact time: 0.9 second.

Table 18 summarizes the results of this test.

TABLE 18

CATALYST: H—ZSM-48 ((M1 − M2/n)/(Si + M1) % = 0.24)

| REACTION CONDITIONS | | | | | |
|---|---|---|---|---|---|
| Temperature (K) | 563, | 601, | 621, | 644, | 673, |
| LHSV (1/hr) | 0.27 | 0.27 | 0.27 | 0.27 | 0.27 |
| Conversion (%) | 60.3 | 100.0 | 100.0 | 100.0 | 100.0 |
| DISTRIBUTION OF PRODUCTS (% by weight) | | | | | |
| Diethylether | 12.0 | 0.0 | 0.0 | 0.0 | 0.0 |
| Acetaldehyde | 0.1 | 0.2 | 0.3 | 0.4 | 0.8 |
| Water | 36.2 | 39.0 | 39.0 | 39.0 | 38.8 |
| Hydrocarbons | 51.7 | 60.8 | 60.7 | 60.6 | 60.4 |
| CO | 0.0 | 0.0 | 0.0 | 0.0 | 0.0 |
| CO$_2$ | 0.0 | 0.0 | 0.0 | 0.0 | 0.0 |
| DISTRIBUTION OF THE HYDROCARBONS (% by weight) | | | | | |
| Methane | 0.0 | 0.0 | 0.0 | 0.0 | 0.0 |
| Ethylene | 99.1 | 99.3 | 99.5 | 99.7 | 99.7 |
| Ethane | 0.0 | 0.0 | 0.0 | 0.0 | 0.0 |
| Propylene + Propane | 0.1 | 0.0 | 0.0 | 0.0 | 0.1 |
| Butanes | 0.0 | 0.0 | 0.0 | 0.0 | 0.0 |
| Butenes | 0.8 | 0.7 | 0.5 | 0.3 | 0.2 |
| Pentanes | 0.0 | 0.0 | 0.0 | 0.0 | 0.0 |
| Pentenes | 0.0 | 0.0 | 0.0 | 0.0 | 0.0 |
| C$_5$+ | 0.0 | 0.0 | 0.0 | 0.0 | 0.0 |
| % iso in C$_4$ | 0.0 | 0.0 | 0.0 | 0.0 | 0.0 |
| % C$_5$+ aromatics | 0.0 | 0.0 | 0.0 | 0.0 | 0.0 |

This table shows an ethylene carbon selectivity of almost 100% by weight and a quantitative conversion rate at a reaction temperature of 601 K.

EXAMPLE 35

Preparation of a H-ZSM-5 (Fe) catalyst having a ratio (M1−M2/n)/(Si+M1) of 0.01%

This catalyst has been prepared in the manner described in example 3, except that an adjusted amount of iron nitrate (Fe(NO$_3$)$_3$.9H$_2$O) has been added to the synthesis mixture instead of Al(NO$_3$)$_3$.9H$_2$O.

The product had the following molar composition: 100 SiO$_2$/Fe(NO$_3$)$_3$; 13 NaOH; 83 TPABr; 13 NH$_4$OH; 662 C$_3$H$_5$ (OH)$_3$.

The solid product obtained has been calcined in the presence of air at 832 K during 12 hours.

The ion exchange has been obtained by refluxing the obtained zeolite in an excess of 0.5N ammonium chloride during 4 hours.

The hydrogen form has been obtained by calcining the catalyst in the reactor itself at a temperature of 673 K under a stream of helium during 1 hour.

According to the results of the atomic absorption, the Si/Fe ratio, in which the iron is tetraedrically bound, or in precipitated or atomic form, was of 100.

Atomic absorption analysis has also shown that this zeolite did not contain aluminium as impurity.

The amount of iron incorporated in the tridimensional network of the zeolite has been determined by E.S.R. after the synthesis and the pretreatment.

The $Fe_O/Fe_T$ ratio, in which $Fe_O$ is the amount of iron which is not bound by tetraedric coordination and $Fe_T$ is the amount of iron incorporated in the framework, has been estimated by integration of the E.S.R. signal, the initial Si/Fe ratio being determined by atomic absorption.

The $Si/Fe_T$ has been determined by the method and the results described by Derouane, E. G.. (Proceedings of Third International Conference on Molecular Sieves, "Molecular Sieves" Sept. 3–7, 1973, Ed. Uytterhoeven, p. 337–342).

The ratio (M1—M2)/(Si+M1) was of 0.01%.

EXAMPLE 36

Conversion of ethanol into ethylene by means of the catalyst of example 35

The reaction conditions were the same as in example 2, except that only the liquid space velocity (LHSV) and the contact time of the reagent have been changed as follows:

LHSV: 0.15 hour$^{-1}$.
Contact time: 0.9 second.

The results of this test are shown in table 19.

TABLE 19

CATALYST: H—ZSM-5 (Fe) (M1 − M2/n)/(Si + M1) % = 0.01

| REACTION CONDITIONS | | | | | | |
|---|---|---|---|---|---|---|
| Temperature (K) | 517, | 527, | 538, | 560, | 569, | 589, |
| LHSV (1/hr) | 0.15 | 0.15 | 0.15 | 0.15 | 0.15 | 0.15 |
| Conversion (%) | 67.6 | 87.4 | 100.0 | 100.0 | 100.0 | 100.0 |
| DISTRIBUTION OF PRODUCTS (% by weight) | | | | | | |
| Diethylether | 13.9 | 1.7 | 0.0 | 0.0 | 0.0 | 0.0 |
| Acetaldehyde | 0.3 | 0.2 | 0.0 | 0.0 | 0.0 | 0.2 |
| Water | 35.6 | 38.6 | 39.1 | 39.1 | 39.1 | 39.0 |
| Hydrocarbons | 50.2 | 59.5 | 60.9 | 60.9 | 60.9 | 60.8 |
| CO | 0.0 | 0.0 | 0.0 | 0.0 | 0.0 | 0.0 |
| $CO_2$ | 0.0 | 0.0 | 0.0 | 0.0 | 0.0 | 0.0 |
| DISTRIBUTION OF THE HYDROCARBONS (% by weight) | | | | | | |
| Methane | 0.0 | 0.0 | 0.0 | 0.0 | 0.0 | 0.0 |
| Ethylene | 100.0 | 99.5 | 99.3 | 99.6 | 99.7 | 99.7 |
| Ethane | 0.0 | 0.0 | 0.0 | 0.0 | 0.0 | 0.0 |
| Propylene + Propane | 0.0 | 0.1 | 0.2 | 0.1 | 0.1 | 0.1 |
| Butanes | 0.0 | 0.0 | 0.0 | 0.0 | 0.0 | 0.0 |
| Butenes | 0.0 | 0.4 | 0.5 | 0.3 | 0.2 | 0.2 |
| Pentanes | 0.0 | 0.0 | 0.0 | 0.0 | 0.0 | 0.0 |
| Pentenes | 0.0 | 0.0 | 0.0 | 0.0 | 0.0 | 0.0 |
| C5+ | 0.0 | 0.0 | 0.0 | 0.0 | 0.0 | 0.0 |
| % iso in $C_4$ | 0.0 | 0.0 | 0.0 | 0.0 | 0.0 | 0.0 |
| % C5+ aromatics | 0.0 | 0.0 | 0.0 | 0.0 | 0.0 | 0.0 |

This table shows that a conversion rate of 100% and an ethylene carbon selectivity of at least 99% by weight have been obtained when the temperature was at least 538 K.

EXAMPLE 37

Preparation of a H-Na-Y catalyst having a molar ratio (M1−M2/n/(Si+M1) of 1.15%

This catalyst has been prepared from a faujasite type zeolite available on the market: Na-Y (Ventron, Si-/Al=2.52).

The zeolite has been calcined and submitted to an ion exchange with the ammonium cation, by heating the catalyst under reflux in a 11.4.10$^{-3}$N (100 ml/g of catalyst) of ammonium chloride during 4 hours.

The hydrogen form has been obtained by calcining this $NH_4$-Na-Y catalyst in the reactor itself at a temperature of 673 K under a stream of helium during 1 hour.

The results of the atomic absorption have shown that the ratio (M1−M2/n)/(Si+M1) of the obtained zeolite was equal to 1.15%.

EXAMPLE 38

Conversion of ethanol into ethylene by means of the catalyst of example 37

A sample of the catalyst of example 37 has been placed in a tubular reactor. The reaction conditions were the same as in example 2, except that the liquid hourly space velocity (LHSV) of ethanol and the contact time of the reagent have been as follows:

LHSV: 0.1 hour$^{-1}$.
Contact time: 0.9 second.

Table 20 shows the operating conditions and the results.

This table shows that a selectivity of ethylene carbon equal to 99% by weight and a quantitative conversion rate are obtained a temperature of 521 K under the reaction conditions mentioned.

TABLE 20

CATALYST: H—Na—Y ((M1 − M2/n)/(Si + M1) % = 1.15)

| REACTION CONDITIONS | | | | | |
|---|---|---|---|---|---|
| Temperature (K) | 494, | 512, | 521, | 529, | 545, |
| LHSV (1/hr) | 0.10 | 0.10 | 0.10 | 0.10 | 0.10 |
| Conversion (%) | 71.6 | 79.8 | 100.0 | 100.0 | 100.0 |
| DISTRIBUTION OF PRODUCTS (% by weight) | | | | | |
| Diethylether | 37.4 | 21.3 | 0.0 | 0.0 | 0.0 |
| Acetaldehyde | 0.0 | 0.0 | 0.0 | 0.0 | 0.0 |
| Water | 30.0 | 33.9 | 39.1 | 39.1 | 39.1 |
| Hydrocarbons | 32.6 | 44.7 | 60.9 | 60.9 | 60.9 |
| CO | 0.0 | 0.0 | 0.0 | 0.0 | 0.0 |
| $CO_2$ | 0.0 | 0.0 | 0.0 | 0.0 | 0.0 |
| DISTRIBUTION OF THE HYDROCARBONS (% by weight) | | | | | |
| Methane | 0.0 | 0.0 | 0.0 | 0.0 | 0.0 |
| Ethylene | 100.0 | 100.0 | 99.5 | 99.6 | 99.6 |
| Ethane | 0.0 | 0.0 | 0.0 | 0.0 | 0.0 |
| Propylene + Propane | 0.0 | 0.0 | 0.0 | 0.0 | 0.0 |
| Butanes | 0.0 | 0.0 | 0.2 | 0.2 | 0.2 |
| Butenes | 0.0 | 0.0 | 0.3 | 0.2 | 0.2 |
| Pentanes | 0.0 | 0.0 | 0.0 | 0.0 | 0.0 |
| Pentenes | 0.0 | 0.0 | 0.0 | 0.0 | 0.0 |
| C5+ | 0.0 | 0.0 | 0.0 | 0.0 | 0.0 |
| % iso in $C_4$ | 0.0 | 0.0 | 40.5 | 44.4 | 43.8 |
| % C5+ aromatics | 0.0 | 0.0 | 0.0 | 0.0 | 0.0 |

EXAMPLE 39

Preparation of a H-Mordenite catalyst having a molar ratio (M1−M2/n)/(Si+M1) of 0.01%

This catalyst has been prepared from a market zeolite: Na-Mordenite (Norton Zeolon 100).

15 g of Na-Mordenite have been added to a 4N nitric acid solution, by using a liquid/solid ratio of 4. The mixture has been stirred during 8 hours at room temperature.

The zeolite has been separated from the solution by filtration, washed with water and dried with air at a temperature of 343 K.

4N nitric acid has been added again to the zeolite with a liquid/solid ratio of 4.

The obtained mixture has been heated to 323 K and stirred at this temperatuyre during 24 hours. The solid product has then been separated from the solution.

The zeolite has then been submitted to a deep bed calcination at a temperature of 853 K during 16 hours.

After this calcination, the treatment with nitric acid was repeated again, except that the liquid/solid ratio was 50 and the mixture was heated under reflux during 24 hours.

The solid product was separated from the solution, washed with water and dried.

Finally, the zeolite was activated by calcining it in the reactor at a temperature of 673 K under a stream of helium during 1 hour.

A H-Mordenite catalyst having a molar ratio $(M_1-M_{2/n})/(Si+M_1)$ of 0.01% has been obtained.

EXAMPLE 40

Conversion of ethanol into ethylene by means of the catalyst of example 39

This test was carried out in the same manner as in example 2, except that the following liquid hourly space velocity (LHSV) of ethanol and contact time of the reagent with the catalyst have been used:

LHSV: 0.07 hour$^{-1}$.

Contact time: 0.9 second.

Table 21 shows the optimum reaction conditions and results.

This table shows that, with this catalyst, an ethylene carbon selectivity at least equal to about 99% by weight and a quantitative (100%) conversion rate are obtained at a temperature of 722 K.

TABLE 21

CATALYST: H—Mordenite $(M_1 - M_{2/n})/(Si + M_1) \% = 0.01$

| REACTION CONDITIONS | | | | | | |
|---|---|---|---|---|---|---|
| Temperature (K) | 588, | 657, | 688, | 698, | 717, | 722, |
| LHSV (1/hr) | 0.07 | 0.07 | 0.07 | 0.07 | 0.07 | 0.07 |
| Conversion (%) | 10.6 | 43.7 | 76.6 | 95.6 | 97.9 | 100.0 |
| DISTRIBUTION OF PRODUCTS (% by weight) | | | | | | |
| Diethylether | 13.6 | 0.0 | 0.0 | 0.0 | 0.0 | 0.0 |
| Acetaldehyde | 0.0 | 0.0 | 0.0 | 0.0 | 0.0 | 0.0 |
| Water | 35.8 | 39.1 | 39.1 | 39.1 | 39.1 | 39.1 |
| Hydrocarbons | 50.6 | 60.9 | 60.9 | 60.9 | 60.9 | 60.9 |
| CO | 0.0 | 0.0 | 0.0 | 0.0 | 0.0 | 0.0 |
| CO$_2$ | 0.0 | 0.0 | 0.0 | 0.0 | 0.0 | 0.0 |
| DISTRIBUTION OF THE HYDROCARBONS (% by weight) | | | | | | |
| Methane | 0.0 | 0.0 | 0.0 | 0.1 | 0.3 | 0.3 |
| Ethylene | 100.0 | 100.0 | 100.0 | 99.6 | 99.1 | 99.1 |
| Ethane | 0.0 | 0.0 | 0.0 | 0.0 | 0.0 | 0.0 |
| Propylene + Propane | 0.0 | 0.0 | 0.0 | 0.3 | 0.6 | 0.6 |
| Butanes | 0.0 | 0.0 | 0.0 | 0.0 | 0.0 | 0.0 |
| Butenes | 0.0 | 0.0 | 0.0 | 0.0 | 0.0 | 0.0 |
| Pentanes | 0.0 | 0.0 | 0.0 | 0.0 | 0.0 | 0.0 |
| Pentenes | 0.0 | 0.0 | 0.0 | 0.0 | 0.0 | 0.0 |
| C$_5$+ | 0.0 | 0.0 | 0.0 | 0.0 | 0.0 | 0.0 |
| % iso in C$_4$ | 0.0 | 0.0 | 0.0 | 0.0 | 0.0 | 0.0 |
| % C$_5$+ aromatics | 0.0 | 0.0 | 0.0 | 0.0 | 0.0 | 0.0 |

EXAMPLE 41

Preparation of a La-ZSM-5 catalyst having a ratio $(M_1-M_{2/n})/(Si+M_1)$ of 1.5%

This catalyst has been prepared as described in example 17.

On a molar basis, the synthesis mixture had the following composition: 60 SiO$_2$/Al$_2$O$_3$; 4 NaOH; 6 TPABr; 666 H$_2$O.

After the hydrothermal crystallisation, the solid product has been separated by filtration, washed with water, dried and calcined in the presence of air, in the manner described in example 17.

The zeolite has then been added to an ammonia solution (pH=8). The mixture has been stirred at room temperature during a few minutes and the solid product has then be separated from the solution and dried.

An ion exchange has been carried out three times by heating the catalyst under reflux in an excess of 0.1N lanthanum nitrate (La(NO$_3$)$_3$ during 4 hours.

The zeolite was then submitted to an ion exchange with the sodium cation, by heating it under reflux in a 16.10$^{-4}$N solution (100 ml/g of catalyst) of sodium chloride during 4 hours.

The results of atomic absorption analysis has shown that the molar ratio $(M_1-M_{2/n})/(Si+M_1)$ of the zeolite was equal to 1.5%.

EXAMPLE 42

Conversion of ethanol into ethylene by means of the catalyst of example 41

The reaction conditions were the same as in example 2, except that the liquid hourly space velocity (LHSV) and the contact time of the reagent were as follows:

LHSV: 0.07 hour$^{-1}$.

Contact time: 0.9 second.

The results of this test and the reaction conditions are summarized in table 22.

A conversion rate of 100% and a ethylene carbon selectivity of at least 99% by weight have been obtained at a reaction temperature of about 498 K under the reaction conditions mentioned.

TABLE 22

CATALYST: La—ZSM-5 $(M_1 - M_{2/n})/(Si + M_1) \% = 1.5$

| REACTION CONDITIONS | | | | | | |
|---|---|---|---|---|---|---|
| Temperature (K) | 408, | 444, | 487, | 490, | 498, | 510, |
| LHSV (1/hr) | 0.07 | 0.07 | 0.07 | 0.07 | 0.07 | 0.07 |
| Conversion (%) | 15.0 | 35.4 | 94.1 | 97.6 | 100.0 | 100.0 |
| DISTRIBUTION OF PRODUCTS (% by weight) | | | | | | |
| Diethylether | 78.6 | 52.8 | 0.3 | 0.0 | 0.0 | 0.0 |
| Acetaldehyde | 0.0 | 0.0 | 0.0 | 0.0 | 0.0 | 0.0 |
| Water | 20.0 | 26.3 | 39.0 | 39.1 | 39.1 | 39.1 |
| Hydrocarbons | 1.4 | 20.9 | 60.7 | 60.9 | 60.9 | 60.9 |
| CO | 0.0 | 0.0 | 0.0 | 0.0 | 0.0 | 0.0 |
| CO$_2$ | 0.0 | 0.0 | 0.0 | 0.0 | 0.0 | 0.0 |
| DISTRIBUTION OF THE HYDROCARBONS (% by weight) | | | | | | |
| Methane | 0.0 | 0.0 | 0.0 | 0.0 | 0.0 | 0.0 |
| Ethylene | 100.0 | 100.0 | 100.0 | 99.7 | 99.5 | 98.5 |
| Ethane | 0.0 | 0.0 | 0.0 | 0.0 | 0.0 | 0.0 |
| Propylene + Propane | 0.0 | 0.0 | 0.0 | 0.3 | 0.5 | 0.8 |
| Butanes | 0.0 | 0.0 | 0.0 | 0.0 | 0.0 | 0.4 |
| Butenes | 0.0 | 0.0 | 0.0 | 0.0 | 0.0 | 0.3 |
| Pentanes | 0.0 | 0.0 | 0.0 | 0.0 | 0.0 | 0.0 |
| Pentenes | 0.0 | 0.0 | 0.0 | 0.0 | 0.0 | 0.0 |
| C$_5$+ | 0.0 | 0.0 | 0.0 | 0.0 | 0.0 | 0.0 |
| % iso in C$_4$ | 36.8 | 0.0 | 0.0 | 0.0 | 0.0 | 59.8 |

TABLE 22-continued

| CATALYST: La—ZSM-5 (M1 − M2/n)/(Si + M1) % = 1.5) | | | | | | |
|---|---|---|---|---|---|---|
| % C$_5$+ aromatics | 0.0 | 0.0 | 0.0 | 0.0 | 0.0 | 0.0 |

We claim:

1. A process for obtaining ethylene from anhydrous or aqueous ethanol by means of a zeolite catalyst containing a silicate of a metal M1 having a valence of 3 and a tetraedric coordination and containing another charge compensating metal M2 selected among the elements of the Ia, Ib, IIa, IIb, IIIa, IIIb, IVa, IVb, Va, Vb VIIb and VIII of the Mendeljev table, said catalyst containing such a proportion of the metal M1 that the molar ratio (M1−M2/n)/(Si+M1), in which n is the valence of said other metal in percents is at most equal to about 1.5, the anhydrous or aqueous ethanol being contacted with said catalyst at such a temperature and contact time that the conversion rate of the ethanol is almost 100% and that the ethylene carbon selectivity is at least equal to about 99% by weight.

2. A process according to claim 1, in which a catalyst containing a metal M1 selected among aluminium, boron, beryllium, chromium, iron and a mixture of aluminium and at least one of the other metals is used.

3. A process according to claim 2, in which the catalyst contains aluminium as metal M1.

4. A process according to claim 2, in which a catalyst free from metal M2 is used.

5. A process according to claim 1, in which the used catalyst has a molar ratio (M1−M2/n)/(Si+M1) comprised between about 0.01 and 1%.

6. A process according to claim 1, in which the used catalyst is a ZSM-5 catalyst, preferably in hydrogen form H-ZMS-5.

7. A process according to claim 1, in which a liquor containing at least 4% by weight of ethanol is reacted on the catalyst.

8. A process according to claim 7, in which the ethanol containing liquor is a liquor of fermentation of a biomass or of a product of synthesis gas derived from coal or petroleum containing ethanol.

9. A process according to claim 4, in which the catalyst contains aluminum as metal M1.

10. A process according to claim 4, in which the used catalyst has a molar ratio (M1−M2/n)/(Si+M1) comprised between about 0.01 and 1%.

11. A process according to claim 4, in which the used catalyst is a ZSM-5 catalyst, preferably in hydrogen form H-ZMS-5.

12. A process according to claim 4, in which a liquor containing at least 4% by weight of ethanol is reacted on the catalyst.

* * * * *